United States Patent [19]
Gillespie et al.

[11] Patent Number: 5,155,018
[45] Date of Patent: Oct. 13, 1992

[54] PROCESS AND KIT FOR ISOLATING AND PURIFYING RNA FROM BIOLOGICAL SOURCES

[75] Inventors: David Gillespie, Glenmoore; Kevin K. Cuddy, Chester Springs, both of Pa.

[73] Assignee: Hahnemann University, Philadelphia, Pa.

[21] Appl. No.: 728,154

[22] Filed: Jul. 10, 1991

[51] Int. Cl.$^5$ .................... C12P 19/34; C12Q 1/68; C07H 15/12; C07H 17/00
[52] U.S. Cl. .......................................... 435/91; 435/6; 435/803; 536/27; 536/28; 536/29; 536/127
[58] Field of Search .............. 435/803, 6, 91; 536/27, 536/28, 29, 127; 514/44

[56] References Cited

PUBLICATIONS

J. Chirgwin et al., Biochemistry, vol. 18, No. 24, pp. 5294–5298 (1979).
B. Vogelstein et al., Proc. Natl. Acad. Sci. USA, vol. 76, No. 2, pp. 614–619 (1979).
R. Boom et al., Journal of Clinical Microbiology, vol. 28, No. 3, pp. 495–503 (1990).

*Primary Examiner*—David L. Lacey
*Assistant Examiner*—Gian P. Wang
*Attorney, Agent, or Firm*—Dann, Dorfman, Herrell and Skillman

[57] ABSTRACT

A process is provided for isolating and purifying biologically active RNA from a biological sources containing RNA, DNA and other cellular materials. The process involves contacting the RNA-containing source with particles comprising siliceous material, such as finely-divided glass, in the presence of a binding solution comprising concentrated, acidified chaotropic salt. Under these conditions, RNA, but not DNA, binds selectively to the siliceous material, and can be separated easily from the other components of the sample. Preferably, the selective binding process is applied to biological cells containing RNA of interest. Intact cells are disrupted by exposing them to a lysing solution comprising, as its main component, concentrated, acidified chaotropic salt. The RNA is then isolated and purified from the lysate using the selective binding process of the invention. The process of the invention may be conveniently provided as a kit, which may include the siliceous material, reagents and instructions for use of the kit to isolate and purify biologically active RNA from biological sources.

17 Claims, No Drawings

PROCESS AND KIT FOR ISOLATING AND PURIFYING RNA FROM BIOLOGICAL SOURCES

BACKGROUND OF THE INVENTION

The present invention relates to isolation, purification and analysis of ribonucleic acid, RNA. In particular, the present invention relates to isolation of RNA from biological sources containing a mixture of biological substances such as proteins, carbohydrates and nucleic acids, and to purification of the isolated RNA.

Ribonucleic acid (RNA), working together with deoxyribonucleic acid (DNA), functions in the control of life processes. In most living organisms, genetic information is stored as DNA, which is a stable, double-stranded polynucleotide. Expression of the genetic information stored in DNA is accomplished by transcription of RNA from a DNA template, followed by translation of the RNA-encoded information into protein.

Gene expression is regulated at both the transcriptional and the translational level. The quantity and characteristics of RNA in a cell is, therefore, an extremely important indicator of gene regulatory events taking place in that cell. As a unit of gene expression, the quantity of a given RNA sequence in cells indicates the level of expression of a given DNA sequence. A great deal of information regarding the physiological state of cells comprising organisms can be gained by determining the presence, quantity, nucleotide sequence and/or structure of a specific RNA. Therefore, purification and analysis of RNA is critical to the study and elucidation of mechanisms by which gene expression is regulated.

Because of the structural similarity between DNA and RNA, previous RNA purification methods have often comprised isolating DNA and RNA together from biological sources. One commonly used method for isolating nucleic acids from cells and tissues was the "Sevag" procedure. This method comprises contacting a cell or tissue homogenate with phenol or a mixture of phenol and chloroform, thereby denaturing proteins and precipitating them while leaving nucleic acids in solution. This method, while still widely used, is hazardous, laborious and of limited utility for isolation of RNA from biological sources containing high amounts of ribonuclease (RNAse), an extremely stable enzyme that degrades RNA.

An improved method for isolating intact RNA from ribonuclease-rich tissues was disclosed by Chirgwin et al., Biochemistry, 18: 5924–29 (1979). This method comprises exposing tissue homogenates to concentrated guanidinium thiocyanate and 2-mercaptoethanol, thereby eliminating nucleolytic degradation of RNA by denaturing all of the cellular proteins, including ribonuclease, at a rate which exceeded the rate of RNA hydrolysis by ribonuclease. Although RNA isolated in this manner was biologically active, it was by no means free of contamination by DNA, protein and other cellular materials. Subsequent, often extensive, manipulation was required to further purify the RNA from other cellular contaminants.

A simple method for purifying DNA from certain sources was disclosed by Vogelstein and Gillespie, Proc. Natl. Acad. Sci (USA), 76: 615–19 (1979). DNA-containing sources were incubated with powdered glass in the presence of a strong solution of the chaotropic salt, sodium iodide (NaI), thereby forming a DNA-glass complex. This technique was adapted for purification of DNA from virtually any source by first treating the source with a solution containing a different chaotropic salt, guanidine thiocyanate (GuSCN).

A similar glass-binding technique was disclosed for co-purification of DNA and RNA from certain biological sources. Boom et al., J. Clin. Micro., 28:495–503 (1990). Cells contained within biological sources, such as serum or urine, were lysed by exposure to strong (greater than 5M) solutions of GuSCN in Tris HCl (pH 8.0), containing 0.2 M EDTA and 2.6% (w/v) Triton X-100. DNA and RNA were copurified from the mixture of biological materials by incubation with diatomaceous earth or silica particles, which formed reversible complexes with the DNA and RNA. While this method was of general utility in isolating nucleic acids from biological sources, it did not provide a means for selectively separating RNA from mixtures containing DNA and RNA together and purifying the RNA thus separated.

From the foregoing, it will be appreciated that a simple, effective means is needed for isolating RNA selectively from biological sources in order to avoid contamination with DNA, which can hinder the purification and subsequent analysis of RNA.

SUMMARY OF THE INVENTION

The present invention provides a simple, effective process for isolating and purifying biologically active RNA from a biological source containing same, which may also include DNA, proteins, carbohydrates and other cellular materials. RNA may be isolated by contacting the RNA-containing source with particles comprising siliceous material, such as finely divided glass or diatomaceous earth, in the presence of a binding solution comprising concentrated, acidified chaotropic salt. Under these conditions, RNA binds selectively to the particulate siliceous material. The particle-bound RNA can be easily separated from the other biological substances contained in the sample. Preferably, the particle-bound RNA is washed to remove nonspecifically adsorbed materials, and the RNA is separated from the particles to which it is bound, e.g., by elution, and the substantially pure, biologically active RNA is recovered.

According to a preferred embodiment of the invention, the selective binding process is applied to biological cells containing RNA of interest. Intact cells are disrupted by exposing them to a lysing solution, which may have as its main component, concentrated chaotropic salt. The lysate contains RNA and other biological substances contained within the cells. The RNA is then isolated and purified from the lysate using the selective binding process of the invention which involves contact with siliceous material in the presence of concentrated acidified chaotropic salt.

According to a further aspect of the invention, an RNA isolation kit is provided for carrying out the process of the invention. The kit typically includes a lysing solution comprising a concentrated chaotropic salt, a binding solution comprising a concentrated, chaotropic salt solution and an acid solution for acidifying the binding solution. Other components of the kit include a suspension of particulate siliceous material, e.g., glass powder, and an eluent for separating RNA from the particle to which it is bound. The kit may optionally include a solution of an inorganic salt in a compatible lower alcohol for washing non-specifically adsorbed substances from the RNA-bound particles and a buffer solution comprising a reducing agent and, if desired, a compatible detergent, e.g., sodium dodecyl sulfate (SDS). The kit may also contain instructions for performing the process of the invention and for preparing the reagents used therein, as well as other accessories useful in carrying out the process.

Thus, the process and kit of the present invention provide a much-needed means for selectively recovering biologically active RNA from cells or other mixtures of biological materials. RNA isolated and purified in this manner may be used for a variety of purposes, such as cloning, amplification, RNA blot analysis and in vitro translation.

DETAILED DESCRIPTION OF THE INVENTION

Sections I-III of the following description detail the preparation and use of a simple, effective method for recovering substantially pure RNA from a mixture of biological substances according to the present invention. Although the process of the invention is described with reference to contacting a biological source of RNA with glass powder in the presence of a binding solution comprising concentrated, acidified chaotropic salt followed by washing and eluting with specific reagents, various alternative particulate binding substrates and reagents may be used, if desired, as will be further described below. The selective binding of RNA to the particulate siliceous material under the conditions described herein facilitates its isolation from the other biological substances contained in the RNA source.

For purposes of the present invention, a chaotropic salt is defined as the salt of a chaotropic agent, which is an agent capable of denaturing proteins. Preferred chaotropic salts for use in the practice of this invention include guanidine thiocyanate, guanidine isothiocyanate and guanidine HCl. Guanidine thiocyanate and guanidine isothiocyanate are especially preferred for use in the invention because both the guanidinium and the thiocyanate ions act as chaotropic agents.

The inventors recognize that guanidine HCl may not be considered to be a chaotropic salt (e.g., see Gillespie, U.S. patent application Ser. No. 07/299,150, at page 81). However, acidifed GuHCl acts to promote selective binding of RNA to siliceous material in biological sources previously prepared with guanidine thiocyanate or sodium perchlorate. In the practice of the present invention, therefore, guanidine HCl is considered to be a chaotrope.

Acidification of a strong chaotropic salt solution enables selective isolation and purification of RNA, rather than co-isolation of DNA and RNA, as was previously done using the glass-binding process described above.

The description which follows sets forth the best mode presently contemplated for practicing the present invention. To the extent that specific materials are mentioned, it is merely for the purposes of illustration and is not intended to limit the invention.

I. Preparation of Materials

A. Preparation of Glass Particle Suspension

According to a preferred embodiment of the invention, glass is used as the siliceous material for selective binding of RNA. Finely divided glass particles may be prepared from any readily-available source of glass or glass fragments. The glass should be clean and free of contaminants. Borosilicate glass is preferred, but not essential, for preparation of glass particles. Particularly good results have been obtained using borosilicate glass scintillation vials for preparation of the glass particle suspension. Other sources of siliceous material, such as diatomaceous earth, are also contemplated for use in the present invention.

To achieve maximum binding of RNA, the glass should be reduced to a fine powder, preferably between 1-100 microns in the longest dimension. This may be accomplished, for example, by grinding glass vials or fragments overnight in a ball mill. In weighing and transferring glass powder, care should be taken to avoid breathing or handling the powder.

The glass powder may be suspended in either distilled water or a chaotropic salt solution of equivalent strength to that which will be used in subsequent steps of the process. The powder is first suspended in distilled water, mixing thoroughly until the suspension is homogeneous. Fine particles are removed by pouring off the supernatant after the suspension has stood for a period of several hours. At this time, the chaotropic salt solution or additional distilled water may be added to the settled powder. The mixing and settling steps are repeated, and the solution is finally transferred to a brown glass bottle for storage. Further details for preparing a glass powder suspension from borosilicate scintillation vials are set forth below in the examples.

B. Preparation of Binding Solution

The binding solution, for selectively binding RNA to the glass particles, comprises an acidified solution of a highly concentrated chaotropic salt. Chaotropic salts contemplated for use in the present invention include, but are not limited to, guanidine HCl, guanidine thiocyanate and guanidine isothiocyanate. In a preferred embodiment, guanidine thiocyanate or guanidine isothiocyanate are used because guanidine and the thiocyanate and isothiocyanate anions both function as chaotropic agents.

The expression "concentrated chaotropic salt solution" as used herein, refers to the working concentration of the chaotropic salt in the binding solution, which should be at least 2M. In a preferred embodiment, the concentration of chaotropic salt is greater than 5M. Highly concentrated stock solutions may be prepared, such that the desired concentration is achieved upon mixing the stock solution with the biological source containing the RNA to be purified.

The binding solution may be acidified with any organic or inorganic acid. In a preferred embodiment, glacial acetic acid is used to acidify the binding solution. The final pH of the binding solution should be between about 2 and 6. A pH value in this range may be attained by incorporating 0.25% glacial acetic acid in the binding solution.

Thus, a preferred binding solution comprises, e.g., 5M guanidine thiocyanate and 0.25% glacial acetic acid. Such an acidified, chaotropic binding solution may be prepared by mixing the stable solutions, 5.9M guanidine thiocyanate and 1.6% glacial acetic acid, in a 100:18 ratio and adding the resulting mixture to a biological source containing RNA to achieve the desired working concentration of chaotropic salt.

C. Preparation of Washing Solution

Following binding of RNA, the glass powder is advantageously washed to remove nonspecifically-adsorbed materials. The washing solution used in this step may comprise a variety of different ingredients. In a preferred embodiment, the washing solution is identical to the binding solution. In other embodiments, the washing solution may comprise lower concentrations of chaotropic salt.

Alternatively, the washing solution may comprise a solution of an inorganic salt, such as lithium chloride, in a compatible lower alcohol, such as ethanol. In a preferred embodiment, the washing solution comprises a 0.4 M lithium chloride solution in ethanol.

D. Preparation of Eluent

RNA is conveniently recovered by elution from the particles to which it is bound. This may be accomplished by incubating the particle-bound RNA in an eluent comprising a dilute salt buffer. Such a solution may comprise, for example, a biological buffer containing 0.5 M sodium chloride. In a preferred embodiment, the eluent further comprises magnesium ions (6 mM), to stabilize the RNA molecules.

Elution of RNA from the glass particles may be further aided by including formamide in the elution solution to disrupt secondary structures which may have formed within the RNA molecules. A preferred embodiment utilizes an eluent comprising up to 50% (v/v) formamide.

Other ingredients may be added to the elution solution to facilitate recovery of intact RNA, free of contaminating DNA molecules. For example, a ribonuclease inhibitor, such as RNAsin (Promega Biotech) may be added to the eluent at appropriate concentrations to inhibit residual ribonuclease activity. Other ribonuclease inhibitors include sodium dodecyl sulfate and various other proteases. Additionally, contaminating DNA molecules may be degraded by including deoxyribonuclease in the eluent.

E. Preparation of Lytic Agent

According to another aspect of the present invention, the selective binding process is applied to previously disrupted biological cells containing the RNA of interest. The cells are disrupted by exposing them to a lytic agent, which comprises as its main component, concentrated, chaotropic salt. The lytic agent may also comprise other agents capable of disrupting cell membranes and inactivating intracellular enzymes. Detergents, such as SDS and sodium lauryl sarcosine, may optionally be used to solubilize cell membranes. Enzyme inactivation will be accomplished primarily by the strong chaotropic salt; however, it may be enhanced by the addition of various thiol reducing agents, such as 2-mercaptoethanol or dithiothreitol.

Use of a nonacidifed lysing solution is advantageous when cell lysates are to be stored, because nonacidifed chaotropic solutions are stable. Biological sources can be prepared directly in binding buffer, which is acidifed, if the RNA extraction process is performed soon thereafter, e.g., the same day.

The concentration of the chaotropic salt in the lysing solution should be at least 2M. Preferably, it is greater than 5M.

Thus, a preferred lysing solution comprises, e.g., 5 M guanidine thiocyanate, 1% (v/v) 2-mercaptoethanol and 5–6% (v/v) sodium lauryl sarcosine.

F. Modifications of Binding, Washing, Elution or Lysis Solutions

Particular cell types of interest may contain ribonucleases which are not fully degraded by the agents comprising the lysing solution. If a recalcitrant ribonuclease is encountered, the above-described solutions may be modified by adding lysozyme, protease K or SDS to any or all of the solutions. Such modifications are described more fully in the examples that follow.

II. Description of the Process and its Applications

The process of the present invention provides a simple, yet very effective means for isolating and purifying RNA from a mixture of biological substances, such as nucleic acids, proteins, carbohydrates and other cellular materials. RNA purified according to the process of the invention is substantially free of DNA contamination, yet is intact and biologically active. Thus, it may be used for a variety of purposes, such as cloning, amplification, RNA blot analysis and in vitro translation.

RNA may be isolated and purified according to the process of the invention from any biological fluid, cell lysate or tissue homogenate. Common sources include, but are not limited to, blood, urine, endocrine fluid tissues, cells, lysates of tissues or cells, etc. The method of the invention may be advantageously applied to intact cells and tissues, such as cultured plant or animal cell lines and excised tissues or whole organs.

Regardless of the source of biological material, all glassware used in the method of the invention should be rendered RNAse free. This may be accomplished by several methods which are commonly used by those skilled in the art. Such methods include autoclaving and/or treatment with diethylpyrocarbonate (DEPC).

Purification of RNA from cells in suspension, i.e., from biological fluids or cell culture, begins as follows. Cells may be pelleted by low-speed centrifugation, followed by resuspension in a lysing solution or directly in an acidified binding solution. Alternatively, a biological fluid may be added to a vessel containing solid chaotropic salt or solid chaotropic salt and acid.

RNA may be purified from intact tissues or organs, such as animal liver or plant leaves, by first mixing intact tissue with lysing or binding solution at a ratio of 10–20 ml solution per gram fresh weight tissue. The mixture is rapidly homogenized, using a hand held homogenizer or an automatic homogenizer, such as a Waring blender, a Polytron tissue homogenizer, or the like. Depending on the tissue, the homogenate may be passed through a coarse filter, such as cheesecloth, to remove large particulate matter. Alternatively, the preparation may be subjected to very low speed centrifugation to sediment particulate material.

After cells are lysed, or tissue homogenized, an appropriate volume of binding solution (i.e., 1–2 volumes) is added to samples of the biological source material, if necessary, followed by the addition of a 1/10–1/5 volume of glass particle suspension. The samples are gently mixed for several minutes, to ensure maximum binding of RNA to the glass particles. Samples are centrifuged briefly to pellet the glass particles then the supernatant is removed and the glass particles are washed with a wash solution. This wash step may be repeated one or more times.

After the wash is completed, the supernatant is removed and RNA is eluted from the glass particles by the addition of the elution solution. The elution step is carried out by gently mixing the glass particles with the elution solution for 10–60 minutes. Samples are again subjected to centrifugation to pellet the glass particles. The supernatant is carefully removed and placed in a separate container.

RNA is precipitated from the supernatant solution by the addition of 2 volumes of ethanol, followed by storage at −40° C. for several hours. Precipitated RNA is pelleted by centrifugation, washed with ethanol, and resuspended in a suitable aqueous buffer. It should be noted that RNA purified by the aforementioned process need not be ethanol precipitated.

It should be appreciated by those skilled in the art that the process of the invention is widely applicable, with minor modifications, to many cell or tissue types. Several variations of the basic method described above are set forth in the examples below. It should be noted that the method is applicable to preparative-scale RNA purification as well as to small scale analytical needs, and may be adapted accordingly.

The following examples are provided to describe the invention in further detail. To the extent that specific materials are mentioned in the examples, this is for purposes of illustration only and not to limit the invention.

III. EXAMPLES

EXAMPLE 1

Preparation of Glass Powder Suspension

Borosilicate glass scintillation vials (Wheaton Corp.) were selected as the source for preparation of the glass particle suspension 100 vials were ground overnight in a ball mill, yielding a fine powder. 50 g of the powder was placed in a large bottle (volume greater than 1 liter), taking proper care to avoid breathing or handling the powder during weighing or transfer. A magnetic stir bar and 1 liter of distilled water were added to the bottle, and the suspension was mixed until all of the glass particles were thoroughly suspended without clumping (mixing up to 2 hours). The suspension was allowed to stand without mixing overnight.

On the following day, the fluid and unsettled glass particles were aspirated and discarded. The approximate volume of the discarded fluid was 970 ml. 200 ml of 5M guanidine thiocyanate (GuSCN) was added to the glass powder, and the suspension was mixed well. The suspension was transferred to a 500 ml brown glass bottle, and allowed to stand overnight. An alternative procedure comprised adding 200 ml of distilled water to the glass powder rather than 200 ml of 5 M GuSCN.

On the following day, the clear supernatant fluid was removed from the suspension leaving approximately 75 ml of suspension at the bottom of the brown glass bottle. The suspension was then transferred to a 100 ml brown glass bottle and stored at room temperature.

EXAMPLE 2

Isolation of RNA from K562 Cells

The following experiment was performed to test the comparative effectiveness of guanidine thiocyanate and guanidine isothiocyanate in lysing solution, binding solution and wash solution.

Two (2) aliquots of $5 \times 10^6$ cells of K562, obtained from the American Type Culture Collection, were pelleted by centrifugation at 2500 rpm for 5 minutes and the media was discarded. The aliquots were labeled A and B. To Tube A was added 0.5 ml of lysing solution A, comprising 5M guanidine thiocyanate (Fluka Chemicals), 0.25% glacial acetic acid and 1% 2-mercaptoethanol. To Tube B was added lysing solution B, comprising 5M guanidine isothiocyanate (Bethesda Research Laboratories), 0.25% glacial acetic acid and 1% 2-mercaptoethanol. The tubes were vortexed to lyse the cell pellets.

Lysates A and B were each divided into four Eppendorf microfuge tubes, 100 ul/tube, and the tubes were labeled A1–A4 and B1–B4.

A binding solution, comprising 0.25% glacial acetic acid and either 5M guanidine thiocyanate (Fluka) or 5M guanidine isothiocyanate (BRL) was prepared. Tubes A1, A2, B1 and B2 received 1 ml of the guanidine isothiocyanate solution. Tubes A3, A4, B3 and B4 received 1 ml of the guanidine thiocyanate solution. The lysed cells and respective binding solutions were mixed thoroughly.

100 ul of glass powder suspension, resuspended in 5 M guanidine thiocyanate (Fluka), without acetic acid, was added to each tube. The samples were mixed for 10 minute. The samples were then centrifuged (microfuge) for 1 minute at 10,000 rpm. The supernatant was removed and discarded.

The glass powder pellets of each sample were washed by adding 1 ml of washing solution as described below: a) tubes A1, A3, B1 and B3 were washed with a washing solution comprising 0.8M LiCl in 50% ethanol; b) tubes A4 and B4 were washed with a washing solution comprising 5 M guanidine thiocyanate (Fluka) and 0.25% glacial acetic acid; c) tubes A2 and B2 were washed with a washing solution comprising 5M guanidine isothiocyanate (BRL) and 0.25% glacial acetic acid. Washing was accomplished by rapping the closed tubes sharply while inverted to dislodge the pellet, followed by mixing for 5 minutes.

Samples were microfuged for 2 minutes at 10,000 rpm, and the supernatant was removed and discarded.

RNA was eluted from the glass powder by adding 200 ul of an elution solution comprising 50% formamide, 0.6 M NaCl and 0.016 M phosphate (pH 7.0). Tubes were rapped sharply to dislodge the pellets, and the suspensions were then mixed for 20 minutes.

Samples were microfuged for 5 minutes and the supernatant was carefully removed and placed in a clean Eppendorf tube.

300 ul of RNase-free water was added to each of the samples which were mixed thoroughly by inverting. RNA was precipitated by adding 1 ml of 100% ethanol to each sample and mixing thoroughly by inverting. Samples were placed in the −40° freezer overnight.

On the following day, precipitated RNA was pelleted by microfuging for 15 minutes. The supernatant was poured off and the RNA pellet was washed with 900 ul of 90% ethanol. The dislodged pellet was re-microfuged for 10 minutes, and the supernatant again removed. The RNA pellet was allowed to dry inverted at 10° C. for 45 minutes.

RNA pellets were resuspended in 100 ul of TBE buffer (0.45M Tris-borate, pH 8, 1 mM EDTA). 10 ul of each sample was removed for analysis by agarose gel electrophoresis, and combined with 5 ul of RNA running dye (TBE with 20% glycerol, containing bromocresol green and bromophenol blue).

Samples were subjected to agarose gel electrophoresis on a 1% agarose gel, which was subsequently stained with ethidium bromide.

Inspection of the stained agarose gel revealed that all procedures tested in the experiment yielded intact RNA. This was judged by the prominent ethidium bromide-staining bands corresponding to 18S and 28S ribosomal RNA and the smear corresponding to messenger RNA from about 6-20S. Thus, intact RNA was obtained using lysing and binding solutions containing either guanidium thiocyanate (Fluka Chemicals) or guanidium isothiocyanate (BRL), and with washing solutions containing lithium chloride-ethanol, 5M guanidine thiocyanate or 5M guanidine isothiocyanate.

EXAMPLE 3

Variations of Basic RNA Isolation Process

An experiment was performed involving a variation on the basic procedure of Example 2, above, and following the protocol of Example 2, comparing GuHCl and GuSCN, without acetic acid, as binding solutions and eliminating the final ethanol precipitation step. Intact RNA was recovered in both cases, as well as when mixtures of GuHCl and GuSCN were used in the binding solution. However, DNA was also recovered when the binding solution was not acidified.

Another experiment was performed involving a variation on the basic procedure of Example 2 and following the protocol of Example 2, comparing a glass suspension stored in $H_2O$ with one stored in 5M GuSCN. Intact RNA was recovered in both cases.

Another experiment was performed involving a variation on the basic procedure of Example 2 and following the protocol of Example 2, using mononuclear cells purified from the blood of a CML patient and comparing a wash solution of 6M $NaClO_4$/0.001MM CDTA/0.05M Tris-HCl, pH=8 with a 1:1 mixture of 0.8M LiCl and ethanol. Intact RNA was recovered in both cases.

Another experiment was performed involving a variation on the basic procedure of Example 2 and following the protocol of Example 2, comparing washing solutions of (1) 6M $NaClO_4$/0.001M CDTA/0.16M $NaPO_4$, pH=7; (2) TBE; (3) $H_2O$ and (4); 0.04M Tris-HCl, pH=8/0.01M NaCl/0.006M $MgCl_2$. Intact RNA was recovered in all cases.

EXAMPLE 4

Isolation of RNA from H9 Cells Using the Process of the Invention

Previous experiments, applying the method of the invention as described in Example 2, were unsuccessful in yielding intact RNA when H9 cells (provided by Dr. Mitchell of Vanderbilt University) were used as the biological source. It was determined that H9 cells contain a guanidine-resistant RNase that is co-extracted with the cellular RNA and degrades the final product during purification. This was shown by performing the experiment described below. RNA was purified from H9 cells, K562 cells and a combination thereof, to determine if the RNA-degrading factor arose from, and was copurified with, the H9 cells. It had previously been determined that intact RNA could be purified from K562 cells, using the method of the invention. The procedure for this experiment is as follows:

15 ml of media containing $5 \times 10^6$ cultured H9 cells, and 15 ml of media containing $5 \times 10^6$ K562 cells, both with good viability were obtained. To sample A, 1.5 ml aliquots of each cell type were added together before centrifugation of the media. To the rest of the samples, 1.5 ml aliquots of the media containing either H9 or K562 cells were centrifuged separately.

Sample A—Cells were combined prior to centrifuging of the media.

Sample B—Cells were pelleted separately and combined after lysing.

Sample C—Cells were pelleted and lysed separately and combined after binding to glass (prior to pelleting of glass).

Sample D—Cells were pelleted, lysed, bound and eluted separately and then combined.

Sample E—H9 cells were carried through the procedure separately.

Sample F—K562 cells were carried through the procedure separately.

Each of the samples A-D contained a total of $1 \times 10^6$ cells. Samples E and F contained only $5 \times 10^5$ cells.

Each sample of cells was collected by centrifugation, and dissolved in 100 μl of lysis buffer (84 μl of 5.9M guanidine thiocyanate; 10 μl of 1M tris-HCl, pH=7.4; 5 μl of 10% N-lauryl sarcosine; and 1 μl of 2-mercaptoethanol.)

2. 800 ul of the binding solution was added to the lysed cells in each of the Eppendorf tubes.

3. 100 ul of the glass slurry was added to the lysed cells and binding solution in each of the Eppendorf tubes.

4. Samples were mixed at room temperature for 10 minutes.

5. Samples were centrifuged for 15 seconds in the microfuge to pellet the glass, and the supernatant was discarded.

6. 800 ul of the washing solution was added to each tube. The tube was inverted and rapped sharply on the table top to dislodge the glass pellets. Samples were mixed gently for 4 minutes.

7. Samples were centrifuged for 1 minute in the microfuge and the supernatants were carefully removed and discarded.

8. 200 ul of elution solution was added to each of the remaining glass pellets (twice the volume of the glass particles). The tubes were inverted and rapped sharply on the table top to dislodge the glass pellets. Samples were mixed for 20 minutes.

9. Samples were centrifuged for 5 minutes in the microfuge and the supernatants carefully removed, while avoiding the transfer of any glass particles. The supernatants were placed in clean 1.5 ml Eppendorf tubes.

10. 300 ul of RNase-free water was added to each supernatant, and the samples were mixed by inverting several times.

11. Each Eppendorf tube was filled with 100% ethanol and mixed by inverting several times.

12. The tubes were placed in a $-40°$ C. freezer overnight.

13. Samples were centrifuged for 15 minutes in the microfuge. Supernatants were removed and discarded, while keeping the pellets in the tubes.

14. 900 ul of 90% ethanol was added to each tube, which were gently inverted several times to mix the pellet.

15. Samples were centrifuged in a microfuge for 15 minutes; supernatants were removed, and pellets were resuspended in TBE buffer 0.45M Tris-borate, pH 8, 1 mM EDTA ).

16. RNA samples were analyzed by agarose gel electrophoresis.

When the glass particles were separately collected by centrifugation and then the preparations were mixed and carried through the remainder of the procedure together, only degraded RNA was obtained. When the H9 and K562 preparations were kept separate throughout the procedure and the final RNA eluates were mixed and analyzed, only degraded RNA was obtained. When the dissolved H9 and K562 biological sources were initially mixed, then taken through the procedure together, only intact RNA was obtained. These results supported the idea that in the case of H9 cells, a ribonuclease became bound to the glass along with the RNA, which was eluted along with the RNA and was capable of degrading the K562 RNA. Molecules in the K562 lysate prevented the binding of the H9 ribonuclease to the glass.

The invention was modified to allow preparation of intact RNA from H9 cells. Lysozyme was added at 10–100 ug/ml to the binding solution and RNA was isolated from H9 cells according to the method of the invention. Intact RNA was obtained. In another experiment, 1% SDS or 200 ug/ml protease K was added to the elution solution and RNA was again purified from H9 cells according to the invention. Again, intact RNA was obtained.

These experiments show that some biological sources may contain a ribonuclease which interferes with isolation of intact RNA. However, this problem can be overcome by including in the binding solution an agent which prevents binding of the ribonuclease to glass or by including a component in the eluent which inhibits ribonuclease action.

EXAMPLE 5

Preparation and Use of RNA Isolation Kit

A kit was prepared for performing the RNA isolation and purification process of the invention. Solutions were prepared for 10 extractions of $10^7$ cells according to the following description.

A stock solution of 5.9M GuSCN (binding solution) was used to make some of the kit components. This solution was made by adding 349 g of solid GuSCN to enough RNase-free $H_2O$ to make 500 ml of solution.

A 100 ml aliquot of the 5.9M GuSCN solution was provided as the binding solution.

An solution of glacial acetic acid was provided as the acidifying solution.

For preparation of the lytic agent, there was provided a buffer solution comprising 1 ml of 1M Tris-HCl, pH=7.4 plus 0.5 ml of 10% sodium lauryl sarcosine plus 0.1 ml of 2-mercaptoethanol.

A suitable wash solution was made up of 50 ml of 0.8M LiCl and 50 ml of ethanol.

An eluent was prepared from 30 ml of 40 mM Tris-HCl, 10 mM NaCl and 6 mM $MgCl_2$.

A glass particle suspension for one kit is 10 ml of glass suspension prepared as described in Example 1, above.

Appropriate instructions for inclusion in the RNA isolation kit are the following:

1. Prepare lytic agent by mixing 0.84 ml of the binding solution and 0.16 ml of the above-described buffer, containing detergent and thiol reducing agent. To a cell pellet of $10^7$ cells in a 25 ml sealable tube, add 1 ml of lytic agent. Vortex to disrupt the cells in the cell pellet.

2. Prepare acidified binding solution by adding 25 μl of acidifying solution to 8 ml of the binding solution. Add 8 ml of the acidified binding solution to the lysed cells.

3. Add 1 ml of glass suspension to the lysed, diluted cells.

4. Mix gently end over end for 10 min.

5. Centrifuge for 1 min at 2500 RPM to pellet the RNA-bound glass particles. Discard the supernatant.

6. Add 8 ml of washing solution. Invert the tube and rap sharply on the benchtop to dislodge the glass pellet.

7. Mix gently end over end for 2–5 min.

8. Centrifuge for 2 min at 2500 RPM to pellet the glass. Carefully remove and discard all of the supernatant.

9. Add 2 ml of eluent. Invert the tube and rap sharply on the benchtop to dislodge the glass pellet.

10. Mix gently end over end for 20 min.

11. Centrifuge for 5 min at 2500 RPM. Carefully transfer the supernatant, containing the purified, biologically active RNA, to a clean test tube.

All of the foregoing steps are to be performed at room temperature unless otherwise specified.

While the isolation and purification of RNA according to the process of the invention has been described and exemplified herein in terms of certain preferred embodiments, various other embodiments will be apparent to those skilled in the art. For example, GuHCl or other chaotrope could be substituted for GuSCN; other particulate binding substrates, e.g., diatomaceous earth may be used in place of glass powder; and other washing solutions or elution solutions could be employed, if desired. Practice of the above-described process is, therefore, not limited to the embodiments actually described and exemplified, but is capable of wide variation and modification without departing from the spirit of the invention, the full scope of which is delineated by the following claims.

What is claimed is:

1. A process for isolating biologically active RNA from a biological source containing said RNA, said process comprising:
    a) contacting said RNA-containing source with particles comprising siliceous material in the presence of an acidified, concentrated chaotropic salt solution, thereby causing RNA present in said source to bind to said particles;
    b) removing said particle-bound RNA from said source; and
    c) separating said biologically active RNA from said particles.

2. The process of claim 1, wherein said biological source is first lysed with a lytic agent.

3. The process of claim 2, wherein said lytic agent comprises a concentrated chaotropic salt.

4. The process of claim 3, wherein said chaotropic salt is guanidine thiocyanate.

5. A process as claimed in claims 1–4, wherein said RNA-containing source is contacted with said particles in the presence of an acidifed, concentrated solution of a chaotropic salt selected from the group consisting of guanidine thiocyanate, guanidine isothiocyanate, guanidine hydrochloride or a mixture of any two or more of said salts.

6. A process as claimed in claims 1–4, wherein said RNA-containing source is contacted with particles of a siliceous material selected from the group consisting of finely divided glass and diatomaceous earth.

7. A process as claimed in claims 1–4, wherein said biologically active RNA is isolated from biological cells as the source of said RNA.

8. A process as claimed in claims 1-4, wherein said acidified chaotropic salt solution is acidifed with acetic acid.

9. A process as claimed in claims 1-4, wherein said RNA is separated from said particles by elution.

10. A process as claimed in claim 9, wherein said RNA is eluted from said particles using an eluent comprising a ribonuclease inhibitor, in an amount effective to inhibit residual ribonuclease activity to which said RNA is exposed.

11. A process as claimed in claim 9, wherein said RNA is eluted from said particles using an eluent comprising deoxyribonuclease, in an amount effective to reduce DNA contamination of said RNA.

12. A process for obtaining substantially pure, biologically active RNA from a mixture containing RNA and DNA, said process comprising:
 a) contacting said mixture with particles comprising siliceous material in the presence of an acidified, concentrated chaotropic salt solution, thereby causing RNA present in said source to bind selectively to said particles to the substantial exclusion of said DNA;
 b) removing said particle-bound RNA from said mixture;
 c) washing said particle-bound RNA;
 d) separating said biologically active RNA from said particles; and
 e) recovering said separated, biologically active, substantially pure RNA.

13. A process as claimed in claim 12, wherein said chaotropic salt solution comprises a chaotropic salt selected from the group consisting of guanidine thiocyanate, guanidine isothiocyanate, guanidine hydrochloride or a mixture of any two or more of said salts.

14. A process as claimed in claim 12, wherein said mixture is contacted with particles of a siliceous material selected from the group consisting of finely divided glass and diatomaceous earth.

15. A kit for isolating and purifying, biologically active RNA present in a biological source containing said RNA, comprising:
 a) a concentrated chaotropic salt solution;
 b) an acid solution for acidifying said salt solution;
 c) a suspension of finely divided glass particles;
 d) an elution solution; and, optionally
 e) a wash comprising a solution of an inorganic salt in a lower alcohol.

16. A kit according to claim 15, which further comprises a buffer solution comprising a thiol reducing agent and, optionally, a compatible detergent.

17. A kit according to claim 15, wherein the components of said kit are provided in single-use aliquots.

* * * * *